(12) United States Patent
Suzuki et al.

(10) Patent No.: US 9,244,079 B2
(45) Date of Patent: Jan. 26, 2016

(54) TESTING METHOD AND TESTING REAGENT FOR ANGIITIS

(75) Inventors: Kazuo Suzuki, Chiba (JP); Toshinori Nakayama, Chiba (JP); Hiroshi Nakajima, Chiba (JP); Tomokazu Nagao, Chiba (JP); Wako Yumura, Tochigi (JP)

(73) Assignees: National University Corporation Chiba University, Chiba (JP); Educational Foundation Jichi Medical University, Tochigi (JP)

( * ) Notice: Subject to any disclaimer, the term of this patent is extended or adjusted under 35 U.S.C. 154(b) by 0 days.

(21) Appl. No.: 13/825,445

(22) PCT Filed: May 12, 2011

(86) PCT No.: PCT/JP2011/060970
§ 371 (c)(1),
(2), (4) Date: Jun. 5, 2013

(87) PCT Pub. No.: WO2012/039161
PCT Pub. Date: Mar. 29, 2012

(65) Prior Publication Data
US 2013/0244259 A1 Sep. 19, 2013

(30) Foreign Application Priority Data
Sep. 22, 2010 (JP) ................................ 2010-212756

(51) Int. Cl.
*G01N 33/53* (2006.01)
*G01N 33/68* (2006.01)
*G01N 33/564* (2006.01)

(52) U.S. Cl.
CPC .......... *G01N 33/6854* (2013.01); *G01N 33/564* (2013.01); *G01N 2800/328* (2013.01)

(58) Field of Classification Search
None
See application file for complete search history.

(56) References Cited

U.S. PATENT DOCUMENTS 6,225,442 B1 5/2001 Wagatsuma et al.

FOREIGN PATENT DOCUMENTS

| JP | 2010-526107 | 7/2010 |
| JP | 2010-527917 | 8/2010 |
| WO | 2008/137835 | 11/2008 |
| WO | 2008/137838 | 11/2008 |

OTHER PUBLICATIONS

Schonermarck et al. (Rhematology 2001, vol. 40, p. 178-184).*
International Preliminary Report on Patentability for PCT/JP2011/060970, dated Apr. 4, 2013, and English translation thereof.
International Search Report for PCT/JP2011/060970, dated Aug. 16, 2011.
Goeken, J., Antineutrophil cytoplasmic antibody—A useful serological marker for vasculitis, J. Clin. Immunol., 1991; vol. 11, No. 4, pp. 61-74.
Kallenberg, C. et al., Autoantibodies vex the vasculature, Nature Medicine, 2008, vol. 14, No. 10, pp. 1018-1019.
Kain, R. et al., Molecular mimicry in pauci-immune focal necrotizing glomerulonephritis, Nature Medicine, 2008, vol. 14, No. 10, pp. 1088-1096., Epub Oct. 5, 2008.
Johnson, P. et al., Up-regulation of the endothelial cell adhesion molecule intercellular adhesion molecule-1 (ICAM-1) by autoantibodies in autoimmune vasculitis, Clin. Exp. Immunol., 1997, vol. 108, pp. 234-242.
Mayet, W. et al., Antibodies to proteinase 3 mediate expression of vascular cell adhesion molecule-1 (VCAM-1), Clin. Exp. Immunol., 1996, vol. 103, pp. 259-267.
De Bandt, M. et al., Antibodies to proteinase-3 mediate expression of intercellular adhesion molecule-1 (ICAM-1, CD54). Br. J. Rheumatol., 1997, vol. 36, pp. 839-846.
Kawakami, T., Immunology Test, 4) Anti-Neutrophil Cytoplasmic Antibody (ANCA), Clinical Dermatology, 2006, vol. 48, No. 10, pp. 1273-1277, and full English translation thereof.
Yoshida, H., Systemic Vasculitis and Various Antibodies, Monthly Respiratory Unit, 2008, vol. 14, No. 4, pp. 327-333.
Saito, R., Diagnosis Standard to be at hand and Its explanation, Microscopic Polyangiitis, Clinical Dermatology, 2004, vol. 46, No. 10, pp. 436-1441.
Kobayashi, S. et al., World trend in vasculitis classification, Angiology, 2009, vol. 49, No. Supplement, p. S94.
Hashimoto, H., Rheumatic disease immunology, inflammation and control thereof, latest findings for treatment of rheumatic disease, recent progress in vasculitis syndromes, Internal Medicine, 2000, vol. 86, No. 2, pp. 332-337.
Ishikawa, Y. et al., A case of anti-moesin antibody/anti-ribosome antibody-positive granulomatous vasculitis in the pelvis to which a steroid was effective, Annual General Assembly and Scientific Meeting of the Japan College of Rheumatology, Program and Abstracts for International Rheumatism Symposium, 2010.03 19, vol. 54th-19th, p. 709, and partial English translation thereof.
International Preliminary Report on Patentability for PCT/JP2011/060970, dated Mar. 26, 2013, and English translation thereof.
Min, Y.S., Study on Serum Proteomics in Patients with Systemic Vasculitis, PhD Thesis Dissertation, I Jan. 2008, pp. I-5.
Suzuki, K. et al., Serology or other Laboratory Methods for Diagnosis, Prognosis or Management—A novel anti-neutrophil antibody of patients with MPO-ANCA-AAV, Clinical and Experimental Immunology, Mar. 30, 2011, 164 (Suppl. 1), pp. 85-99.

(Continued)

*Primary Examiner* — Jacob Cheu
(74) *Attorney, Agent, or Firm* — Dickinson Wright PLLC

(57) ABSTRACT

[Problem] The present invention provides a novel pathological marker of angiitis which serves as an alternative to MPO-ANCAs.
[Means for Solution] According to one embodiment of the present invention, a method for testing angiitis which includes a step of detecting an antibody specifically recognizing a moesin in a biological sample is provided. In addition, according to another embodiment of the present invention, a reagent for testing angiitis which contains a substance that detects an antibody specifically recognizing a moesin in a biological sample is provided.

4 Claims, 8 Drawing Sheets

(56) References Cited

OTHER PUBLICATIONS

Guilpain, P. et al., Pathogenic effects of antimyeloperoxidase antibodies in patients with microscope polyangiitis, Arthritis & Rheumatism, vol. 56, No. 7, Jan. 1, 2007, pp. 2455-2463.

Suzuki, K. et al., A novel autoantibody against moesin in the serum of patients with MPO-ANCA-associated vasculitis, Nephrology Dialysis Transplantation, Dec. 5, 2013, pp. 1-10.

Extended European Search Report for EP 11826607.1, dated Feb. 18, 2014.

Japanese Official Notice of Reason for Refusal dated Jun. 2, 2015, including English translation, 8 pages, PJ No. 2012-534948.

* cited by examiner

CBB staining

Verification of specific reaction

← Band of moesin

Verification by Western blotting

Pt A: anti-M high/MPO-ANCA low
Pt B: anti-M low/MPO high

TESTING METHOD AND TESTING REAGENT FOR ANGIITIS

TECHNICAL FIELD

The present invention relates to a novel method of testing angiitis and a novel reagent for testing the same.

BACKGROUND ART

Neutrophil antibodies to myeloperoxidase (MPO), (MPO-ANCAs: Anti-Neutrophil Cytoplasmic Antibodies), are associated with intractable angiitis such as crescent-forming nephritis, microscopic polyangiitis (MPA) and allergic angiitis (AGA, Churg-Straus Syndrome (CSS)). Further, since the MPO-ANCA titer in the serum of patients with these diseases correlates to the disease activity, MPO-ANCAs are used as specific markers of these diseases in the diagnosis and assessment of treatments (see, for example, Non-patent Document 1).

However, even when a MPO-ANCA is used as a marker, the titer of the MPO-ANCA in serum does not always agree with the pathology. Thus, it has been suggested that MPO-ANCA is not a sole factor which induces angiitis by acting on neutrophils and plays a role after the onset of angiitis and there rather may be other molecule or mechanism which induces angiitis. Accordingly, in recent years, discussions have been made with regard to the possibility that there is a target molecule of autoantibody other than neutrophil MPO. Consequently, there have been reports on involvement of several target molecules such as Lamp2 (see Non-patent Documents 2 and 3). In addition, attempts have been made to elucidate the activation mechanism of vascular endothelial cells by autoantibodies including MPO-ANCA as a mechanism for onset of angiitis and pathological development. To this day, it has been reported that the serums of angiitis patients showing positive for an autoantibody induce the expression of ICAM-1 in human umbilical vein endothelial cells (HUVECs) (see Non-patent Document 4) and that the anti-proteinase-3 autoantibody (PR3-ANCA) of Wegener's granulomatosis patients induces the expressions of ICAM-1 and VCAM-1 (see Non-patent Documents 5 and 6). However, there has been no report with regard to the direct effects of a MPO-ANCA on vascular endothelial cells. Therefore, it is still unclear as to whether or not a molecule other than MPO-ANCAs and Lamp2 antibodies is involved in the pathology of angiitis. Furthermore, since reactions caused by anti-mouse MPO antibody (rmMPO antibody) are observed in the same manner also in a MPO-deficient mouse, it has been suggested that a molecule other than MPO serves as a target in vascular endothelial cells. Moreover, although it has been reported that the serums and autoantibodies of angiitis patients activate HUVECs, the pathogenicity thereof and the acting molecule have not been clarified.

In addition, the present inventors have reported that an anti-rmMPO antibody (MPO-ANCA) activates mouse glomerular endothelial cells (mGECs). However, it is still unclear with regard to the factors that play a role in the pathology of angiitis other than MPO-ANCAs and Lamp2 antibodies.

Thus, at present, while there are suggestions on the presence of other factors that are involved in the pathology of angiitis in addition to MPO-ANCAs that are clinically used in diagnosis and the like of angiitis, the essence of such factors is not clear. As described in the above, the diagnosis and assessment of treatments by MPO-ANCAs do not necessarily perfectly reflect the actual pathology; therefore, identification of the factors other than MPO-ANCAs can potentially complement the diagnosis and the like by MPO-ANCAs or provide a novel clinical marker which serves as an alternative and it is of extreme significance in terms of clinical medicine. Here, the present inventors discovered protein M as a factor other than MPO-ANCAs.

PRIOR ART DOCUMENTS

Non-Patent Documents

[Non-patent Document 1] Goeken J A. Antineutrophil cytoplasmic antibody—A useful serological marker for vasculitis. J Clin Immunol 1991; 11: 61-74.

[Non-patent Document 2] Kallenberg C G, Stegeman C A, Heeringa P. Autoantibodies vex the vasculature. Nat. Med. 2008 October; 14(10): 1018-9.

[Non-patent Document 3] Kain R, Exner M, Brandes R, Ziebermayr R, Cunningham D, Alderson C A, Davidovits A, Raab I, Jahn R, Ashour O, Spitzauer S, Sunder-Plassmann G, Fukuda M, Klemm P, Rees A J, Kerjaschki D. Molecular mimicry in pauci-immune focal necrotizing glomerulonephritis. Nat. Med. 2008 October; 14(10): 1088-96. Epub 2008 Oct. 5.

[Non-patent Document 4] Johnson P A, Alexander H D, McMillan S A, Maxwell A P. Up-regulation of the endothelial cell adhesion molecule intercellular adhesion molecule-1 (ICAM-1) by autoantibodies in autoimmune vasculitis. Clin Exp Immunol, 1997; 108: 234-242.

[Non-patent Document 5] Mayet W J, Schwarting A, Orth T, Duchmann R, Meyer zum Buschenfelde K H. Antibodies to proteinase 3 mediate expression of vascular cell adhesion molecule-1 (VCAM-1). Clin Exp Immunol 1996; 103: 259-267.

[Non-patent Document 6] De Bandt M, Meyer O, Hakim J, Pasquier C. Antibodies to proteinase-3 mediate expression of intercellular adhesion molecule-1 (ICAM-1, CD 54). Br J Rheumatol 1997; 36: 839-846

SUMMARY OF THE INVENTION

Problem to be Solved by the Invention

In view of the above-described prior art, an object of the present invention is to provide a novel pathological marker of angiitis which serves as an alternative to MPO-ANCAs.

Means for Solving the Problem

The present inventors intensively studied in order to solve the above-described problem and discovered that, surprisingly, an autoantibody to a moesin (hereinafter, also referred to as "MO-ANCA") induces inflammation by acting on moesin in glomerular endothelial cells and activating the cells. Further, based on this discovery, the present inventors analyzed the reactivity of the MO-ANCA existing in the serums of angiitis patients and found that the reactivity of the MO-ANCA does not completely, but rather does not at all correlate with that of MPO-ANCA, to discover that angiitis can be subclassified based on the reactivity of the MO-ANCA in serum and then completed the present invention.

In this manner, according to the studies carried out by the present inventors, the above-described protein M was identified to be moesin. This moesin (membrane-organizing extension spike protein) is a protein isolated from a bovine uterus and it has been suggested that moesin may serve as a receptor protein of heparan sulfate (Lankes, W. T. et al., The Biochemical Journal 1988; 251: 831-842). In addition, by cDNA cloning, it has been shown that human moesin normally consists of 577 amino acids (Lankes, W. T. et al., Proc. Natl. Acad. Sci. U.S.A., 1991; 88: 8297-8301). However, it is not known at all that an antibody specifically recognizing this moesin is found in the serums of angiitis patients.

That is, according to the first embodiment of the present invention, a method for testing angiitis which includes a step of detecting an antibody specifically recognizing a moesin in a biological sample is provided. In the testing method, it is preferred that the biological sample be a serum sample and the antibody be an autoantibody to a moesin. The above-described testing method may further include a step of detecting an antibody specifically recognizing myeloperoxidase (for example, MPO-ANCA) in the above-described biological sample.

Further, the angiitis to be tested by the above-described testing method is preferably microscopic polyangiitis (MPA), allergic granulomatous angiitis (Churg-Strauss syndrome (CSS)), Wegener's granulomatosis, Guillain-Barré syndrome, thrombotic thrombocytopenic purpura (TTP), idiopathic thrombocytopenic purpura, IgA nephropathy, rapidly progressive glomerulonephritis, idiopathic interstitial pneumonia, sarcoidosis, diffuse panbronchiolitis, Behçet's disease, systemic lupus erythematosus (SLE), Sjögren's syndrome, Takayasu's disease (aortitis syndrome), Buerger's disease, polyarteritis nodosa, malignant rheumatoid arthritis, temporal arteritis, antiphospholipid antibody syndrome, scleroderma, eosinophilic fasciitis or pemphigus. The angiitis is more preferably microscopic polyangiitis (MPA), allergic granulomatous angiitis (Churg-Strauss syndrome (CSS)) or Wegener's granulomatosis, most preferably MPA.

Further, according to the second embodiment of the present invention, a reagent for testing angiitis which includes a substance that detects an antibody specifically recognizing a moesin in a biological sample is provided. In the testing reagent, it is preferred that the above-described substance be a moesin and/or a partial peptide thereof. It is also preferred that the testing reagent further include a labeled secondary antibody which recognizes the above-described antibody.

Effects of the Invention

According to the present invention, a novel pathological marker of angiitis which serves as an alternative to MPO-ANCAs can be provided. Further, for example, by using the novel angiitis marker provided by the present invention (such as anti-moesin antibody) in combination with a conventionally known angiitis marker, MPO-ANCA, it becomes possible to subclassify the pathologies of angiitis and assess the treatment effects based on the information on the presence or absence of correlation with angiitis pathology, the quantitative values of the markers and the like.

MODE FOR CARRYING OUT THE INVENTION

Figure 1:
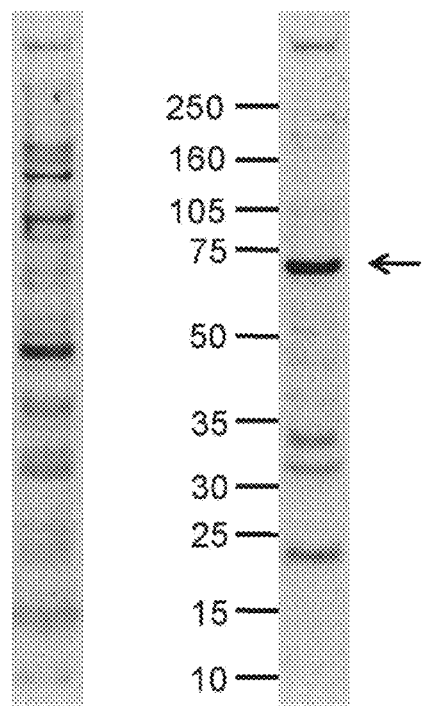
FIG. 1 shows the results of Western blotting which was performed in Example in order to verify the expression of moesin in mGECs.

The first embodiment of the present invention is a method for testing angiitis which includes a step of detecting an antibody specifically recognizing a moesin in a biological sample.

The subject to which the testing method of the present invention can be applied is not particularly restricted as long as it is an animal, and examples thereof include mammals. The mammals are not particularly restricted and examples thereof include primates, laboratory animals, domestic animals and pets, more specifically human, monkey, rat, mouse, rabbit, horse, cow, goat, sheep, dog and cat. Preferably, the subject animal is human.

The biological sample which may be used in the method of the present invention is not particularly restricted and examples thereof include tissues, cells, cell extracts and body fluids that are originated from the animal to be tested. Examples of the tissues include those of a spleen, lymph node, kidney, lung, heart and liver, and examples of the cells include splenocytes, lymphocytes, neutrophils, monocytes, macrophages, dendritic cells and antibody-producing cells. Further, examples of the body fluids include blood, serum, plasma, urine, sweat and spinal fluid. Considering the ease of detection and the like, the biological sample is preferably a body fluid, particularly serum, plasma or urine.

The specific mode of "angiitis" to be test by the testing method of the present invention is not particularly restricted and it includes all of the diseases, symptoms and impairments that may be recognized as "angiitis" in the art. Examples of such angiitis include, but not limited to, microscopic polyangiitis (MPA), Wegener's granulomatosis, allergic granulomatous angiitis (AGA) and CSS. However, the testing method of the present invention is used primarily for microscopic polyangiitis (MPA) and CSS, more preferably MPA.

Moesin, which is recognized by the antibody detected in the testing method of the present invention (hereinafter, may be referred to as "anti-moesin antibody"), is a protein belonging to a family of proteins that are generally bound to cytoskeleton (Ezrin Radixin Moesin: ERM Family) and, in human, moesin normally consists of 577 amino acids. The moesin is not particularly restricted as long as it is originated from the above-described mammals; however, it is preferably a moesin of human origin. Examples of human moesin include a protein having the amino acid sequence of GenBank Accession No. NM002444 and naturally-occurring allelic variants thereof.

The class of the antibody is not particularly restricted and it may be any of, for example, IgG, IgD, IgE, IgA, sIgA and IgM. Further, the term "antibody" also encompasses binding fragments thereof (such as Fab, Fab' and F(ab')$_2$) as long as they specifically bind to a moesin.

The antibody detected in the present invention is preferably an autoantibody which specifically recognizes autologous moesin. For example, in cases where the biological sample is of human origin, preferably, a human antibody which specifically recognizes human moesin is detected. In such a case, it is particularly preferred that the biological sample be a serum sample. Since a moesin contains a sequence part which cross-reacts with MPO in some cases, the antibody may also be a part of a MPO-ANCA.

As a method of detecting the antibody which specifically recognizes a moesin in a biological sample, a known method is used, and it is not particularly restricted. For example, a method in which a reaction occurring in a liquid phase or a solid phase (such as antigen-antibody reaction) is directly measured or a method in which inhibition of immunoreaction is measured by an addition of an inhibitory substance is used.

Examples of the above-described methods include a method in which a specific binding of an antibody to moesin or a partial peptide thereof in a biological sample is directly or indirectly detected by bringing the moesin or a partial peptide thereof into contact with the biological sample.

The moesin to be used in the above-described method is not particularly restricted as long as it is one of the above-described moesin proteins and can be specifically recognized by an anti-moesin antibody which is an autoantibody of the animal to be tested; however, the moesin is preferably one originated from the animal to be tested. For example, when the test subject is human, it is preferred to use a human moesin (such as a protein having the amino acid sequence of GenBank Accession No. NM002444 or a naturally-occurring allelic variant thereof).

Further, in the present invention, the length of a partial peptide of moesin is not particularly restricted as long as the partial peptide contains an antigenic determinant which is recognized by the anti-moesin antibody detected in the present invention. In general, an antigenic determinant of a protein antigen is constituted by at least 5 to 6 amino acid residues; therefore, in the present invention, a moesin partial peptide containing at least 5, preferably not less than 8, more preferably not less than 10 amino acid residues can be used.

The moesin or partial peptide thereof may be modified as well. Examples of such modification include modifications by phosphoric acid, a sugar, a sugar chain, a phospholipid, a nucleotide or the like.

The moesin or partial peptide thereof used in the present invention can be obtained from human or other animals described in the above by a known method. For example, moesin can be purified from a moesin-expressing tissue such as spleen, uterus or kidney, a cultured cell thereof or a moesin-expressing cell strain such as UT-7. Specifically, after homogenizing a tissue or cells of an animal, extraction thereof is performed with an acid or the like and the resulting extract can be subjected to a combination of chromatographies such as reverse phase chromatography and ion exchange chromatography, thereby moesin can be purified and isolated.

The moesin or partial peptide thereof according to the present invention can also be produced by culturing a transformant introduced with an expression vector that contains nucleic acids encoding a moesin or a partial peptide thereof so as to produce the moesin or partial peptide thereof and then separating and purifying the thus produced moesin or partial peptide thereof from the resulting culture.

The moesin or partial peptide thereof used in the present invention can also be produced by a known peptide synthesis method. The peptide synthesis method may be any of, for example, solid-phase synthesis methods and liquid-phase synthesis methods. The moesin or partial peptide thereof can be produced by performing condensation between a partial peptide or amino acids capable of constituting a moesin and a residual part thereof and then, when the resulting product contains a protecting group, eliminating the protecting group.

The moesin or partial peptide thereof used in the present invention can also be produced by cleaving a moesin obtained by any one of the above-described or below-described methods with an appropriate peptidase.

The moesin or partial peptide thereof may also be bound with an appropriate tag in order to make the purification operations and the like easy. Examples of such tag include immunoglobulin Fc regions, maltose-binding proteins (MBP), glutathione-S-transferase (GST), c-Myc tags, FLAG tags, HA tags and His tags.

The method for detecting the antibody is not particularly restricted and more specific examples thereof include the following methods:

(1) an agglutination reaction method in which a moesin or a partial peptide thereof (antigen) is coated on the surface of blood cells or gelatin particles and a biological sample is then added thereto, thereby inducing antigen-antibody reaction to form aggregates;

(2) a double immunodiffusion method (DID: Ouchterlony method) in which an extract containing a moesin or a partial peptide thereof and a biological sample are dispersed in an agar gel to induce precipitation reaction;

(3) methods in which, after immobilizing a purified moesin or a partial peptide thereof onto a plate and then adding thereto a biological sample to allow it to react with the thus immobilized moesin or partial peptide thereof, i) a secondary antibody bound with an enzyme is further allowed to react and the resulting substrate coloration is detected using a spectrophotometer (ELISA method);

ii) a secondary antibody bound with a fluorescent dye is further allowed to react and the resulting fluorescence is measured (fluoroimmunoassay: FIA); or iii) a secondary antibody bound with a chemiluminescent substance is further allowed to react and the resulting chemiluminescence is measured (chemiluminescence immunoassay: CLIA);

(4) methods in which a moesin or a partial peptide thereof is coated on the surface of latex particles or glass beads and a solution of agglutination products formed by an encounter between the particles and an antibody is then irradiated with light, followed by measurement of the transmitted light (turbidimetric immunoassay) or measurement of the scattering light (immunonephelometry);

(5) radio immunoassay in which a moesin or a partial peptide thereof is labeled with a radioisotope and then allowed to react with a biological sample, followed by detection of antigen-antibody reaction;

(6) a fluorescent antibody method in which, after attaching a thin frozen section or cells of a tissue containing a moesin or a partial peptide thereof onto a glass slide and dropping thereon a biological sample to allow reaction to take place, a secondary antibody bound with a fluorescent dye is further allowed to react and the resulting fluorescence is then detected under a microscope;

(7) a surface plasmon resonance analysis method in which a moesin or a partial peptide thereof is immobilized onto a chip and a biological sample is poured thereon to assess the affinity; and (8) Western blotting method in which, after transferring a moesin or a partial peptide thereof separated and developed in a gel by electrophoresis onto a nitrocellulose film or the like, the biological sample is allowed to react with the resultant and antigen-antibody reaction is detected.

For example, in cases where the detection means is an ELISA method, specifically, detection and/or quantification can be performed in the following manner. That is, in accordance with a commonly used ELISA method, for example, a biological sample is loaded to each well of a multi-well plate coated with a moesin or a partial peptide thereof and, after adding an enzyme-labeled secondary antibody to each well to allow reaction to take place, an enzyme substrate is further added thereto and the product formed by the enzyme are detected and/or quantified, thereby the antigen-antibody reaction can be detected and/or quantified.

In the case of the above-described ELISA method, the enzyme used for labeling may be any enzyme commonly used in an ELISA method, and examples of such enzyme include peroxidase, alkaline phosphatase, β-D-galactosidase, glucose oxidase, luciferase, esterase and β-D-glucuronidase. From the point of view for attaining more sensitive and stable detection, peroxidase or alkaline phosphatase is preferably used. Further, the enzyme substrate can be selected as appropriate depending on the enzyme used. For example, when the enzyme is peroxidase, 3,3',5,5'-tetramethylbenzidine or the like is used, and when the enzyme is alkaline phosphatase, sodium p-nitrophenyl phosphate or the like is used.

The product produced by the enzyme can be detected and/or quantified by measuring the absorbance of the product. For example, in cases where 3,3',5,5'-tetramethylbenzidine is used as the enzyme substrate, the absorbance may be measured at 655 nm.

For example, in cases where the detection means is fluoroimmunoassay (FIA), examples of the fluorescent dye include FITC (fluorescein isothiocyanate), PE (phycoerythrin), APC (allophycocyanin), Cy-3 and Cy-5.

Further, for example, in cases where the detection means is chemiluminescence immunoassay (CLIA), examples of the chemiluminescence include acridinium ester.

When an antibody specifically recognizing a moesin was detected in a biological sample, we can judge that the subject from whom the biological sample originated is highly likely to experience a symptom of angiitis or already have angiitis. In such a case, it can be also considered that the higher the titer of the antibody specifically recognizing a moesin in the biological sample, the more likely that the subject will have a symptom of angiitis or already have angiitis. On the other hand, when the antibody specifically recognizing a moesin is not detected in a biological sample, it can be judged that the subject from whom the biological sample originated is not likely to experience a symptom of angiitis or already have angiitis.

When judging the likelihood of experiencing a symptom of the disease, the criteria for the judgment are not necessarily restricted to detection or non-detection of such antibody. For example, in cases where a cut-off value is set to be an average ±3 SD of the amount of an antibody specifically recognizing a moesin in a biological sample originated from a healthy subject, when the measured amount of the antibody is not less than the cut-off value, the subject may be judged to be highly likely to experience a symptom of angiitis or already have angiitis, while when the amount is not higher than the cut-off value, the subject may be judged to be not likely to experience a symptom of angiitis or already have angiitis.

Furthermore, when the testing method of the present invention detected an antibody specifically recognizing a moesin in a patient who has been found to have angiitis based on the presence/absence of blood MPO-ANCA, the amount thereof or other indicators, it can be determined that the patient is likely to be presenting a symptom or relapse of angiitis or a weakness of the therapeutic effect. In other words, it can be also said that the testing method according to the first embodiment of the present invention may further include a step of detecting an antibody which specifically recognizes myeloperoxidase (MPO) in a biological sample. Here, examples of the above-described antibody include MPO-ANCAs. As for the detection method thereof, since those modes that are described in the above in relation to the detection of an antibody specifically recognizing a moesin are applicable, detailed description is omitted here.

As described in the above, by detecting each of an antibody specifically recognizing a moesin (autoantibody to moesin) and an antibody specifically recognizing myeloperoxidase (MPO) (autoantibody to MPO (MPO-ANCA)), the pathologies of angiitis can be subclassified. That is, by the present invention, "use of an autoantibody to a moesin as a reactive pathological marker of angiitis, which is characterized by, for subclassification of angiitis, detecting each of an autoantibody to a moesin and an antibody specifically recognizing myeloperoxidase" can also be provided. Here, the angiitis to be subclassified is not particularly restricted and the above-described angiitides and other conventionally known angiitides may be the subject of subclassification. Examples thereof include complications of angiitis in a small vessel and angiitis in a medium artery. Examples of such angiitides include those which are caused by allergic granulomatous angiitis (Churg-Strauss syndrome; CSS), Wegener's granulomatosis (WG), microscopic polyangiitis (MPA), Kawasaki disease, rheumatoid arthritis, SLE and Behçet's disease. Thereamong, the above-described two antibodies are each preferably used as a reactive pathological marker of angiitis for the purpose of subclassifying the pathologies of microscopic polyangiitis, allergic granulomatous angiitis (Churg-Strauss syndrome (CSS)) or Wegener's granulomatosis (particularly, microscopic polyangiitis). Particularly, the above-described two antibodies may also be effectively used as pathological markers for assessing the remission, relapse or therapeutic resistance caused by a treatment of angiitis.

Furthermore, when an antibody which specifically recognizes moesin was detected, the following angiitis-induced symptoms and disorders are suspected and, therefore, once a more detailed causal relationship is elucidated, such an antibody will be extremely useful as a pathological marker for assessing the remission, relapse or therapeutic resistance caused by treatments of these symptoms and disorders: cardiovascular diseases (such as hypertension, cerebral infarction, myocardial infarction, apoplexy and aneurysm), multiple sclerosis, Guillain-Barré syndrome, chronic inflammatory demyelinating polyneuropathy, lysosomal storage disease, idiopathic thrombosis, thrombotic thrombocytopenic purpura (TTP), idiopathic thrombocytopenic purpura, IgA nephropathy, rapidly progressive glomerulonephritis, intractable nephrotic syndrome, idiopathic interstitial pneumonia, sarcoidosis, diffuse panbronchiolitis, autoimmune hepatitis, Behçet's disease, systemic lupus erythematosus (SLE), Sjögren's syndrome, Takayasu's disease (aortitis syndrome), Buerger's disease, polyarteritis nodosa, malignant rheumatoid arthritis, temporal arteritis, antiphospholipid antibody syndrome, scleroderma, eosinophilic fasciitis and pemphigus.

Further, according to the second embodiment of the present invention, a reagent for testing angiitis which contains a substance that detects an antibody specifically recognizing a moesin is provided.

The above-described "substance" contained in the testing reagent of the present embodiment is not particularly restricted as long as it is capable of detecting an antibody specifically recognizing a moesin in the above-described method. The "substance" is preferably moesin or a partial peptide thereof. Further, in cases where the anti-moesin antibody detected in the present invention is an antibody group which recognizes a plurality of antigenic determinants, from the standpoint of improving the detection sensitivity by allowing the plurality of antigenic determinants existing in moesin to exhaustively detect the antibodies specifically recognizing the respective antigenic determinants, the above-described substance is preferably moesin (the full length of the protein).

The moesin or a partial peptide thereof may be provided in the form of, for example, powder or a solution. Alternatively, the moesin or a partial peptide thereof may also be provided in the form of being supported on an insoluble carrier such as blood cell, gelatin particle, plate, latex particle, glass bead, glass slide, chip, microtiter plate, centrifuge tube, microbead, membrane or paper disc. Here, in the case of a carrier on a container, the moesin or a partial peptide thereof is supported on the part which is in contact with the solution supported on the carrier and, in the case of, for example, a microtiter plate, the moesin or a partial peptide thereof is supported on the well part. The moesin or a partial peptide thereof can be supported on an insoluble carrier by a known method.

By using the testing reagent of the present invention, angiitis can be easily tested by the above-described method. The testing reagent of the present invention can also be provided in an angiitis testing kit which further contains a reagent and the like that are used in the above-described detection method. Specific examples of the above-described reagent and the like include buffers that are used to dilute a reagent and/or a biological sample, fluorescent dyes, reaction vessels, positive control, negative control and instruction manuals describing the test protocol. These elements may also be combined in advance as required. By using this kit, the testing of angiitis according to the present invention can be easily performed; therefore, the kit is extremely useful for determining the therapeutic stage in the early stage.

EXAMPLES

The present invention will now be described in detail by way of examples thereof; however, the present invention is not restricted to the following examples.

1. Culture of Mouse Glomerular Endothelial Cells (mGECs)

From a C57BL/6 mouse, mGECs were isolated to be used. For maintenance of the cells, a culture supernatant of confluent cells was removed and washed with PBS. Then, after adding 1 ml of trypsin/PBS (Gibco) and heating the resultant for about 5 minutes, cells were detached by gentle tapping. Subsequently, the cells were recovered, diluted with a culture medium and then cultured on a collagen-coated 10-cm φ culture dish (Iwaki) at 37° C. in a 5% $CO_2$ incubator. Here, as the culture medium, RPMI-1640 (Sigma) [containing 10% inactivated FBS (Sigma), 5 ng/ml vascular endothelial growth factor (VEGF) (Peprotech), 10 ng/ml epidermal growth factor (EGF) (Sigma), 10 ng/ml fibroblast growth factor basic (bFGF) (Sigma), 20 U/ml heparin (Ajinomoto), 1 μg/ml hydrocortisone (Sigma), 50 U/ml penicillin and 50 μg/ml streptomycin (Gibco)] was employed.

2. Preparation of Rabbit Anti-Recombinant Mouse Myeloperoxidase Antibody (Rabbit Anti-rmMPO Antibody)

*Escherichia coli* was transformed with a plasmid containing MPO cDNA of a mouse (C57BL/6) and cultured in accordance with a conventional method. Then, a mouse MPO (rmMPO), an expressed recombinant protein, was recovered. This rmMPO consists of His tag-labeled L chain-H chain of mouse MPO. Then, a rabbit was immunized with a purification product of the thus obtained rmMPO, and IgG fraction of the resulting polyclonal antibody was isolated from serum using protein A, thereby obtaining an anti-rmMPO IgG. Here, a rabbit IgG used as a control was obtained in the same manner as described in the above, except that the immunization with the rmMPO was not performed.

3. Detection of Band Formed by mGEC Molecules Reacting with Anti-rmMPO Antibody 3.1 Preparation of Cell Lysate The mGECs cultured in the above 1. were recovered using a cell scraper in PBS and made into a pellet by centrifugation. After washing the thus obtained pellet cells with PBS, the cells were dissolved in a RIPA buffer (150 mM NaCl, 10 mM Tris-HCl, 0.1% SDS, 1.0% Triton X-100, 1.0% sodium deoxycholate and 5 mM EDTA) and then disrupted by sonication to obtain a cell lysate.

3.2. Blotting

After gently washing a nitrocellulose membrane obtained in the above 3.1 with 0.05% Tween 20/TBS [50 mM Tris-HCl/150 mM NaCl (pH7.6)], blocking thereof was performed with 5% BSA/0.05% Tween 20/TBS at 4° C. overnight. Then, the treated membrane was allowed to react with a primary antibody (buffer: 5% BSA/0.05% Tween 20/TBS) at room temperature for 1.5 hours. Subsequently, the membrane was washed with 0.05% Tween 20/TBS three times and then allowed to react with an HRP-labeled secondary antibody (buffer: 5% BSA/0.05% Tween 20/TBS) at room temperature for 1.5 hours. Thereafter, the treated membrane was washed with 0.05% Tween 20/TBS three times and then allowed to react with an ECL solution (GE Healthcare) for 1 minute. Finally, the membrane was exposed to an X-ray film (GE Healthcare) in a dark room and developed using a developing machine (Fujifilm). The results are shown in FIG. 1. As shown in FIG. 1, a moesin of 68 kDa was detected, so that moesin was confirmed to be expressed in the mGECs.

4. Two-Dimensional Electrophoresis

4.1 Preparation of Cell Lysate

The mGECs cultured in the above 1. were recovered using a cell scraper in PBS and made into a pellet by centrifugation. After washing the thus obtained pellet cells with PBS, the cells were dissolved in a RIPA buffer (150 mM NaCl, 10 mM Tris-HCl, 0.1% SDS, 1.0% Triton X-100, 1.0% sodium deoxycholate and 5 mM EDTA) and then disrupted by sonication to obtain a cell lysate.

4.2 First Dimension Isoelectric Focusing

To the cell lysate obtained in the above 3.1, a sample buffer (Invitrogen) was added to a final concentration of 50%. As the gel, an IEF gel pH 3-10 (Invitrogen) was employed. After loading this gel to an electrophoresis chamber (Invitrogen), an anode buffer (Invitrogen) and a cathode buffer (Invitrogen) were poured into the lower and upper layers, respectively, and 15 µL of the sample was applied. Isoelectric focusing was performed at 100 V for 1 hour, at 200 V for 1 hour and then at 500 V for 30 minutes. Here, as a marker, an IEF marker (Serva) was applied.

4.3 Two-Dimensional SDS-PAGE

Figure 2:
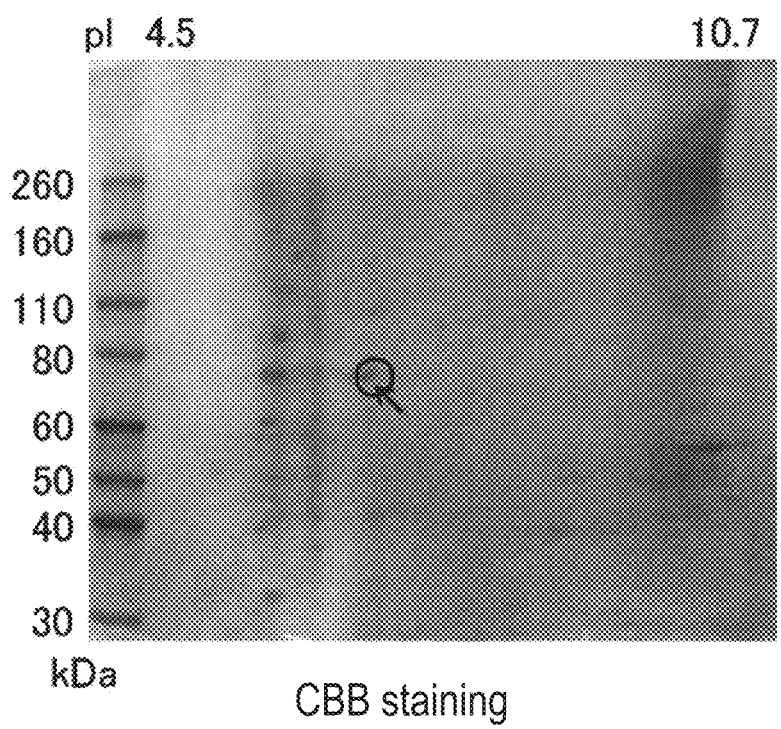
FIG. 2 shows the result of CBB staining of a gel which was performed in Example after two-dimensional electrophoresis.

The gel isoelectrically focused in the above 3.2 was fixed with 12% TCA for 30 minutes. Then, after washing the resulting gel with DDW twice, the gel was stained with Coomassie Brilliant Blue (CBB) in accordance with the procedures of SimplyBlue™ SafeStain (Invitrogen). The thus stained gel was washed with DDW and then shaken in 20% ethanol for 10 minutes twice. Subsequently, a lane of the gel through which the sample was allowed to move was cut out and shaken for 5 minutes in 20% ethanol/2× sample buffer. Thereafter, the resulting gel was gently washed with a running buffer (Invitrogen) and then loaded to a well of a SDS-PAGE gel to perform SDS-PAGE at 200V for about 1 hour and 15 minutes. Here, as a marker, Novex (registered trademark) Sharp Protein Standard (Invitrogen) was employed. The result of the CBB staining is shown in FIG. 2. After the below-described Western blotting and subsequent development, the spot circled in FIG. 2 was cut out using a scalpel and used in the below-described PMF analysis.

5. Western Blotting

5.1 Transfer from SDS-PAGE Gel to Nitrocellulose Membrane

The gel which was subjected to SDS-PAGE in the above 3.2 was loaded to a transfer apparatus (Invitrogen) along with a nitrocellulose membrane (GE Healthcare) to perform transfer at 30V for 1 hour.

5.2.1 Blotting

Figures 3, 4:
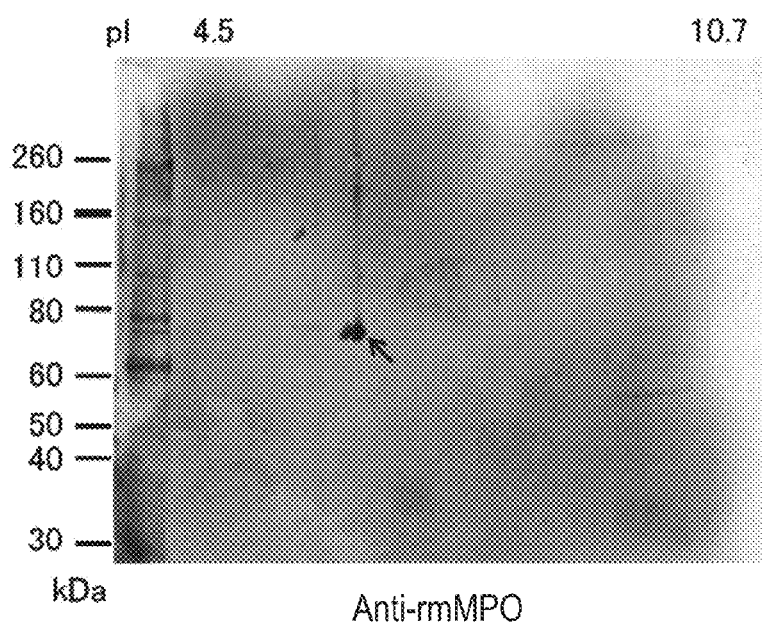
FIG. 3 shows the result of Western blotting which was performed in Example after two-dimensional electrophoresis.
FIG. 4 shows the results of TOF-MS analyses that were performed in Example for a spot (gel) which was cut out after the CBB staining shown in FIG. 2.

After gently washing the nitrocellulose membrane obtained in the above 5.1 with 0.05% Tween 20/TBS [50 mM Tris-HCl/150 mM NaCl (pH7.6)], blocking thereof was applied with 5% BSA/0.05% Tween 20/TBS at 4° C. overnight. Then, the treated membrane was allowed to react with a primary antibody (buffer: 5% BSA/0.05% Tween 20/TBS) at room temperature for 1.5 hours. And then, the membrane was washed with 0.05% Tween 20/TBS three times and then allowed to react with an HRP-labeled secondary antibody (buffer: 5% BSA/0.05% Tween 20/TBS) at room temperature for 1.5 hours. Thereafter, the treated membrane was washed with 0.05% Tween 20/TBS three times and then allowed to react with an ECL solution (GE Healthcare) for 1 minute. Finally, the membrane was exposed to an X-ray film (GE Healthcare) in a dark room and developed using a developing machine (Fujifilm). The result of the development is shown in FIG. 3. As shown in FIG. 3, there was observed a spot at a molecular weight of 67 kDa and a pI of 6.2.

It is noted here that, throughout this Example, as the antibodies, the following ones were used.

Primary antibody: anti-rmMPO antibody (5 µg/ml), control rabbit IgG (5 µg/ml), rabbit anti-human moesin monoclonal antibody (Abcam; 1 µg/ml) and rabbit anti-human moesin polyclonal antibody (Upstate; 1 µg/ml)

Secondary antibody: HRP-labeled anti-rabbit IgG antibody (Sigma; 1/20,000 dilution)

6. PMF (Peptide Mass Fingerprint) Analysis and Homology Analysis of Amino Acid Sequences

6.1 Identification of mGEC Molecule Reacted with Anti-rmMPO Antibody

The spot (gel) which was cut out from the gel subjected to the two-dimensional electrophoresis and subsequent CBB staining in the above 4.3 was analyzed by TOF-MS. The results thereof are shown in FIG. 4. Based on the results shown in FIG. 4, the protein contained the spot was identified as moesin.

6.2 Estimation of Molecular Binding Between Anti-rmMPO Antibody and Moesin

Then, in order to estimate the molecular binding between the anti-rmMPO antibody and moesin, for the amino acid sequences of moesin and MPO, homology search was performed using Protein BLAST. As a result of the search, there were found five similar sequences. Further, the sequences having the highest similarity were generally found to have six amino acids.

7. Effects of Anti-Moesin Antibody on Signal Transduction Of Vascular Endothelial Cell (Cell ELISA)

Then, by the following method (Cell ELISA method), a hypothesis that an anti-moesin antibody has an effect of promoting the expression of ICAM-1 in vascular endothelial cells in the same manner as anti-rmMPO antibody (MPO-ANCA) was examined.

That is, the mGECs cultured in the above 1. were inoculated to a collagen-coated 96-well plate (Iwaki) at a concentration of $4 \times 10^3$ cells/well. After one-day incubation, the cells were washed with warm RPMI-1640 containing 1% FBS (test medium). Then, the test medium was freshly added and the cells were cultured for 1 hour. Subsequently, an antibody used for cell stimulation and TNF-α were diluted with the test medium and added to the wells to culture the cells for another 6 hours. Thereafter, the cells were washed with PBS three times and fixed with 0.2% glutaraldehyde at 4° C. for 5 minutes. Using Dulbecco's phosphate-buffered saline-0.05% Tween 20 containing bovine serum albumin (BSA) (Sigma, code: 30-5450-5; PEST; 1% BSA/PBST), non-specific binding was blocked, and 0.5 µg/ml of a rat anti-mouse ICAM-1 monoclonal antibody (eBioscience) was then added and allowed to react with the cells for 1.5 hours at room temperature. For color development, 1-Step™ Turbo TMB-ELISA (Pierce) was employed. After quenching the reaction with 0.5M sulfuric acid (Wako Pure Chemical Industries), the absorbance was measured at a wavelength of 450 nm to quantify the cells.

Here, cell was stimulated by using the following antibodies:

Rat anti-mouse moesin monoclonal antibody (Sanko Junyaku; 10 µg/ml), anti-rmMPO antibody (100 µg/ml), control rabbit IgG (100 µg/ml) and control rat IgG2a (R&D systems; 10 µg/ml).

As a result of the above-described test, it was confirmed that the expression of ICAM-1 was promoted by the anti-moesin antibody; therefore, the above-described hypothesis was proved.

8. Confirmation of the Presence of Anti-Moesin Antibody in Serum of Angiitis Patient By the following method (Western blotting method), it was confirmed that the antibody reacting with moesin contained in a human lung epithelial cell A549 lysate was an anti-moesin antibody.

8.1 Western Blotting

Figure 5:
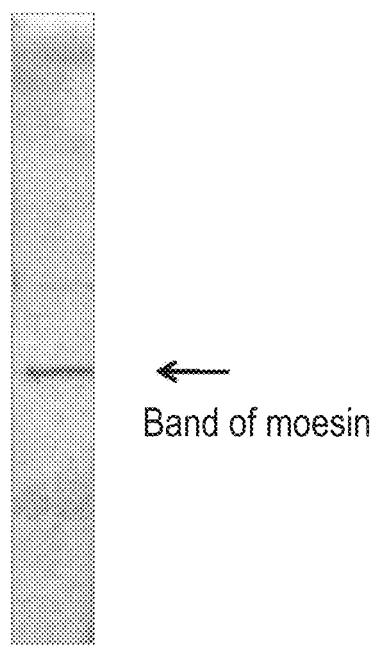
FIG. 5 shows the result of Western blotting performed in Example by using an anti-moesin antibody (MO-ANCA) as a primary antibody, by which results it was confirmed that the anti-moesin antibody contained in the serum of an ANCA-related angiitis patient showing positive for MPO-ANCA recognizes moesin protein.

A nitrocellulose membrane obtained in the same manner as in the above 3.1 using a human lung epithelial cell A549 lysate was gently washed with 0.05% Tween 20/TBS [50 mM Tris-HCl/150 mM NaCl (pH7.6)] and blocking thereof was performed with 5% BSA/0.05% Tween 20/TBS at 4° C. overnight. Then, the treated membrane was allowed to react with plasma of a patient, which had been 50-fold diluted with a buffer (5% BSA/0.05% Tween 20/TBS), at room temperature for 1.5 hours. Subsequently, the membrane was washed with 0.05% Tween 20/TBS three times and then allowed to react with an HRP-labeled secondary antibody (anti-human IgG antibody; buffer: 5% BSA/0.05% Tween 20/TBS) at room temperature for 1.5 hours. Thereafter, the treated membrane was washed with 0.05% Tween 20/TBS three times and then allowed to react with an ECL solution (GE Healthcare) for 1 minute. Finally, the membrane was exposed to an X-ray film (GE Healthcare) in a dark room and developed using a developing machine (Fujifilm). As a result, there was observed a band corresponding to human moesin protein; therefore, it was confirmed that the serum of the angiitis patient contained an anti-moesin antibody. Here, by Western blotting method in which this anti-moesin antibody was used as a primary antibody, it was confirmed that the anti-moesin antibody (MO-ANCA) contained in the patient's serum recognizes moesin protein (FIG. 5).

9. Quantification of Anti-Moesin Antibody Contained in Serum of Angiitis Patients By the following method (ELISA method), plasma of a patients suffering from intractable angiitis, which is MPO-ANCA-related angiitis, was analyzed.

Figure 6:
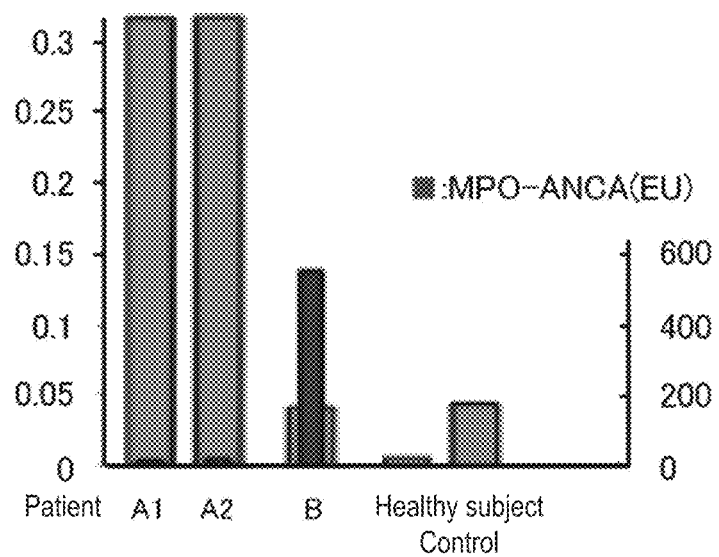
FIG. 6 is a graph showing the results that were obtained in Example by quantifying an anti-moesin antibody (MO-ANCA) and MPO-ANCA in serum samples collected from ANCA-related angiitis patients showing positive for MPO-ANCA.

9.1 Quantification of Anti-Moesin Antibody Contained on Plasma of Angiitis Patients by ELISA Method A recombinant human moesin was diluted with a carbonate buffer to a concentration of 0.2 μg/well (50 μL, 2 mg/ml) and coated onto the wells of a 96-well plate. After one-day incubation, the cells were washed with PBST (PBS-0.1% Tween20) twice and then blocked with 100 μL of 1% BSA/PBST for 1.5 hours, followed by two washings with PBST. Then, after adding plasma of a patient or healthy subject which had been 50-fold diluted with 1% BSA/PBST, the treated plate was left to stand for 1.5 hours at room temperature and then washed with PBST twice. Thereafter, an AP-labeled anti-human IgG antibody was added and the treated plate was left to stand for another 1.5 hours at room temperature. After washing the plate with PBST twice, the cells were allowed to react with an AP substrate buffer and the absorbance was measured at a wavelength of 405 to 650 nm for quantification. The results are shown in FIG. 6. As shown in FIG. 6, the serum of the patients suffering from MPO-ANCA-related angiitis contained an anti-moesin antibody (MO-ANCA). It is noted here that the "MPO-ANCA" was also simultaneously quantified in the same manner as described in the above and the results thereof are also shown in FIG. 6. Here, in FIG. 6, "PtA: anti-M high/MPO-ANCA low" corresponds to two patients (A1 and A2) whose results are indicated by the two bars in the left and these patients had a large amount of anti-moesin antibody and a small amount of MPO-ANCA. Meanwhile, in FIG. 6, "Pt B: anti-M low/MPO high" corresponds to a patient whose results are indicated by the bar to the right of the above-described two bars and this patient had a small amount of anti-moesin antibody and a large amount of MPO-ANCA. Further, in FIG. 6, the rightmost two bars correspond to the results for control healthy subjects.

10. Subclassification of Angiitis by MO-ANCA and MPO-ANCA

Figure 7:
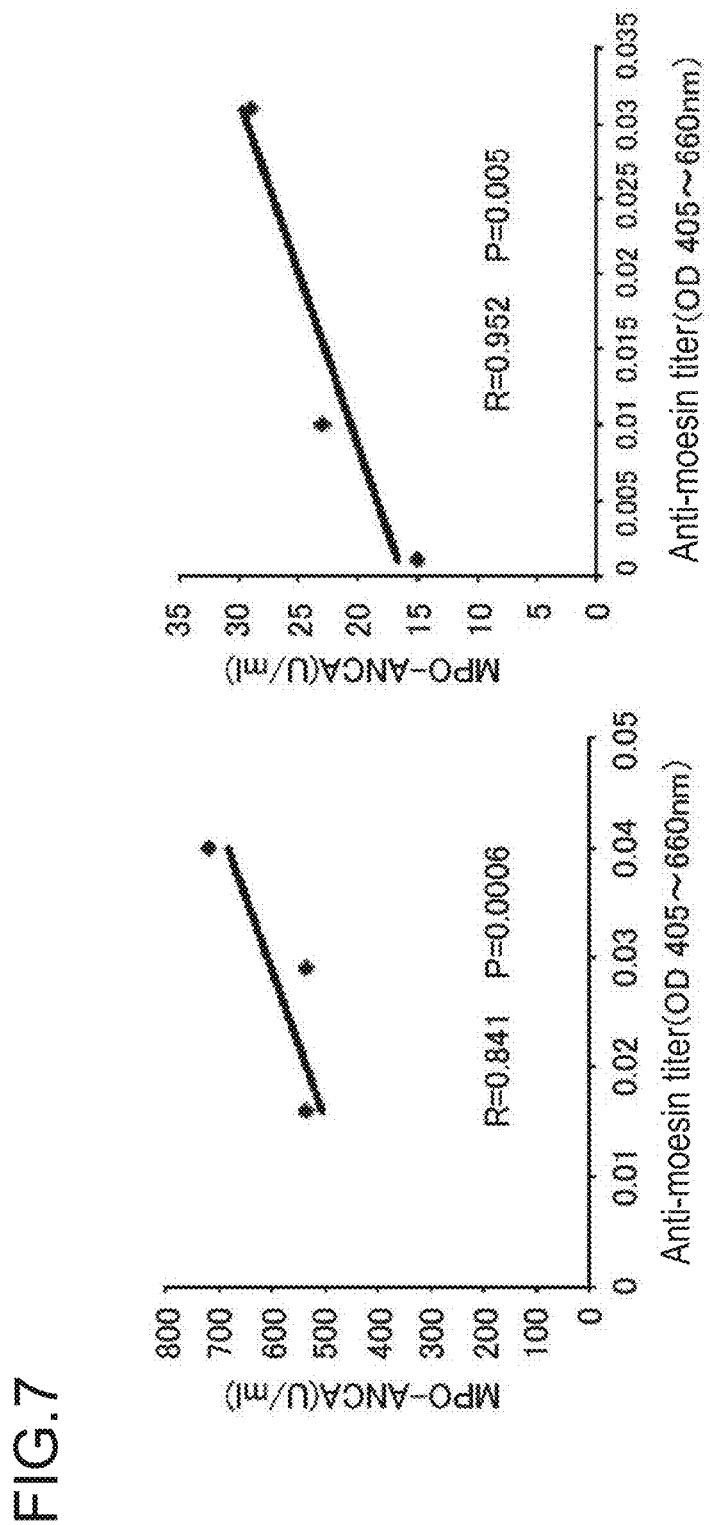
FIG. 7 is graphs showing the results of analyses that were performed in Example with regard to the relationship between the quantitative analysis of an anti-moesin antibody (MO-ANCA) and those of a MPO-ANCA in patients' serum samples.
Figure 8:
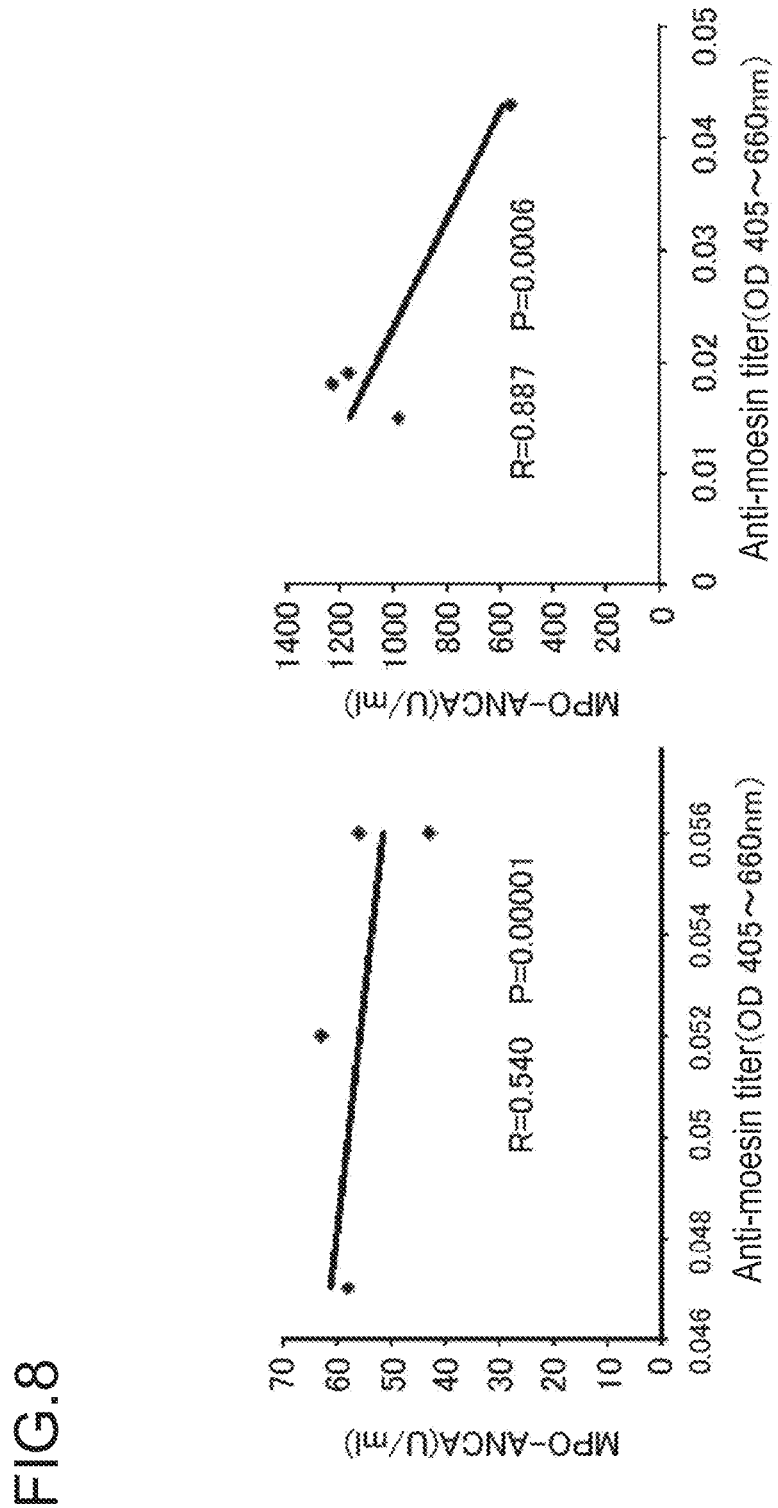
FIG. 8 is graphs showing the results of analyses that were performed in Example with regard to the relationship between the quantitative analysis of an anti-moesin antibody (MO-ANCA) and those of a MPO-ANCA in patients' serum samples.

The relationship between the quantification results of anti-moesin antibody (MO-ANCA) and those of MPO-ANCA in the patients' serum samples was analyzed. As a result, as shown in the above-described FIG. 6 and FIGS. 7 and 8, founded on the respective quantification results, it was discovered that, the pathologies of angiitis can be classified into 4 groups of: (1) pathology where there is a positive correlation between anti-moesin antibody (MO-ANCA) and MPO-ANCA (FIG. 7); (2) pathology where there is a negative correlation between anti-moesin antibody (MO-ANCA) and MPO-ANCA (FIG. 8); (3) pathology where anti-moesin antibody (MO-ANCA) has a high value (positive) but MPO-ANCA has a low value (negative) (Pt-A shown in FIG. 6); and (4) pathology where MPO-ANCA has a high value but anti-moesin antibody (MO-ANCA) has a low value (Pt-B shown in FIG. 6). Accordingly, by utilizing and combining this finding of the present invention with the existing test results based on MPO-ANCA, a novel standard for subclassification of angiitis such as MPA can be provided. In addition, by using such a subclassification standard, the pathologies of angiitis and the effects of various treatments therefor can be more precisely classified based on the presence or absence and the amount of MO-ANCA and MPO-ANCA in the patient's serum. Moreover, ultimately, such a novel standard contributes to institution of better treatment regimen and improvements in the prognosis of patients.

11. Multiple Comparison Based on MPO-ANCA Titer and Anti-Moesin Antibody Titer

In the same manner as described in the above 9.1 (ELISA method), the MPO-ANCA titer and the anti-moesin antibody titer in the plasma of angiitis patients (n=76) were measured and they were subjected to multiple comparison. The results thereof are shown in FIG. 9.

Figure 9:
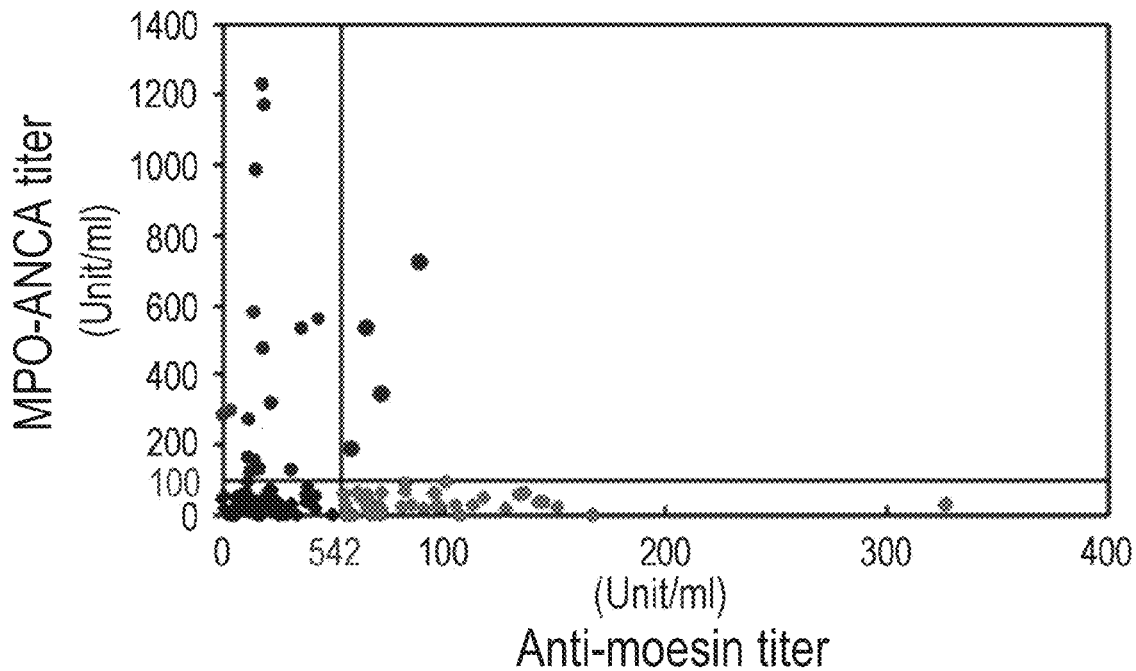
FIG. 9 is a graph showing the results that were obtained in Example by measuring the MPO-ANCA titer and anti-moesin antibody titer in the plasmas of angiitis patients by an ELISA method and performing multiple-comparison on the measurements.

As shown in FIG. 9, most of the patients who exhibited a high MPO-ANCA titer or positive for anti-moesin antibody had a high value for only either of these features and there were only 4 patients who exhibited a high MPO-ANCA titer and positive for anti-moesin antibody. From these results, it was suggested that the cross-reaction between the anti-moesin antibody and MPO-ANCA is very weak. In this manner, the present invention provides a novel means for testing angiitis which is different from conventional technologies utilizing MPO-ANCA; therefore, it can be said that the present invention is a technology which is extremely advantageous in clinical medicine.

12. The Relationship Between the MPO-ANCA and Anti-Moesin Antibody Titers and Various Clinical Test Values For those angiitis patients whose MPO-ANCA titer and anti-moesin antibody titer were measured in the above 11., the serum creatinine value was measured by a conventional method. Then, for each of the 4 regions shown in FIG. 9, the thus obtained serum creatinine values were compared. The results are shown in FIG. 10.

Figure 10:
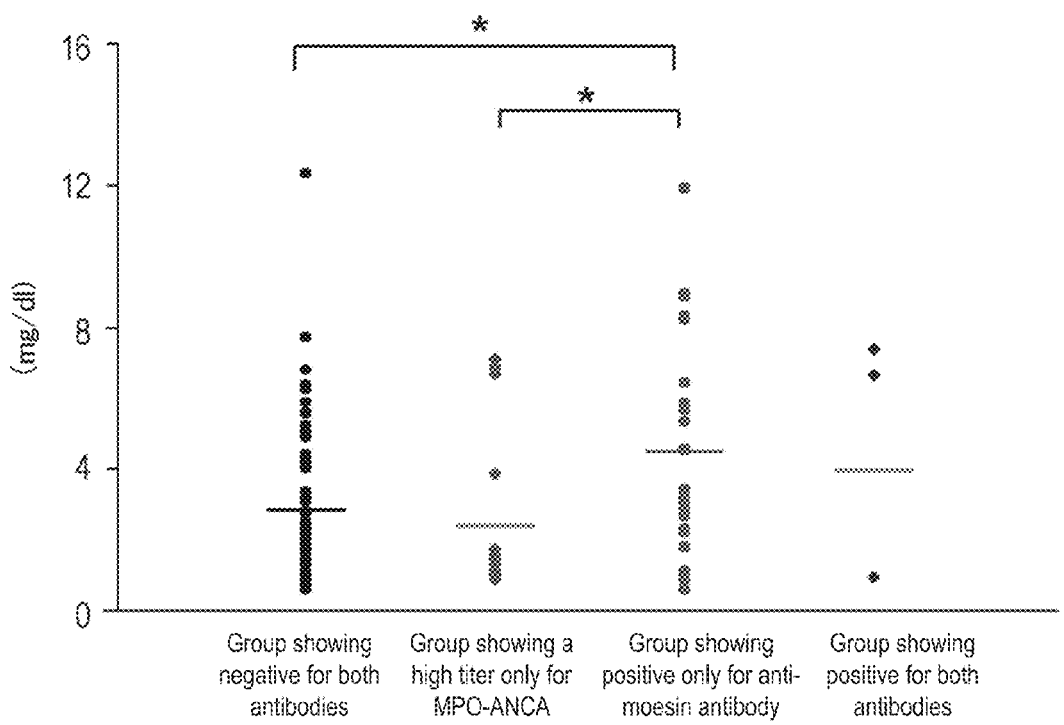
FIG. 10 is a graph showing the results that were obtained in Example by measuring the serum creatinine values of angiitis patients, for whom the MPO-ANCA titer and anti-moesin antibody titer were measured in the course of investigating the relationship between the MPO-ANCA and anti-moesin antibody titers and various clinical test values in Example, and comparing the thus obtained serum creatinine values for each of the 4 regions shown in FIG. 9.

As shown in FIG. 10, the group showing positive only for anti-moesin antibody exhibited a significantly higher serum creatinine value as compared to the group showing negative for both antibodies and the group showing a high titer only for MPO-ANCA.

In the same manner, among those angiitis patients whose MPO-ANCA titer and anti-moesin antibody titer were measured in the above 11., for the group showing a high titer only for MPO-ANCA and the group showing positive only for anti-moesin antibody, the aspartate aminotransferase (AST) value, urea nitrogen (BUN) value and lactate dehydrogenase (LDH) value in serum were measured by a conventional method. The thus obtained values were compared between the two groups and then statistically processed by Kruskal-wallis test and Tukey test. The results are shown in Table 1 below.

TABLE 1

|  | AST | BUN | LDH |
|---|---|---|---|
| Group showing positive only for anti-moesin antibody | ↑** | ↑* | ↓* |
| Group showing a high titer only for MPO-ANCA | ↓** | ↓* | ↑* |

**There was a significant difference (significance level: 1%)
*There was a significant difference (significance level: 5%)

According to the results shown in Table 1, in the group showing positive only for anti-moesin antibody, as compared to the group showing a high titer only for MPO-ANCA, the serum AST and BUN values were significantly higher, while the serum LDH value was significantly lower. Taking these results into consideration along with the above-described measurement results of the serum creatinine value, it was suggested that the anti-moesin antibody plays a role in the reduction of renal function in angiitis patients.

13. Measurement of the Cytokine and Chemokine Production by Neutrophils of Healthy Subject Upon Stimulation with Anti-Moesin Antibody Since the anti-moesin antibody was found to react with neutrophils, the production profiles of cytokines and chemokines were measured upon stimulation of neutrophils with the anti-moesin antibody, and the reaction to the stimulation of neutrophils with the anti-moesin antibody was analyzed in vitro.

First, neutrophils were isolated from a plasma sample taken from a healthy subject and suspended in 10% FBS/RPMI at a concentration of $2 \times 10^6$ cells/ml.

Then, 100 μL of the thus obtained neutrophil suspension was inoculated in each well of a 96-well plate. Thereafter, 100 μL of a mouse monoclonal anti-moesin 2287 antibody (20 μg/ml) was added to each well and, after incubating the plate in a $CO_2$ incubator at 37° C. for 24 hours, the treated plate was centrifuged at 1,000×g and 20° C. for 10 minutes to recover supernatants.

Using the thus obtained supernatants, the production amounts of various cytokines and chemokines were measured using a multiple cytokine assay kit (Bio-Plex). As for a control group, the same experiment was carried out using a mouse monoclonal antibody IgG2a in place of the mouse monoclonal anti-moesin 2287 antibody. The results are shown in FIG. 11.

Figure 11:
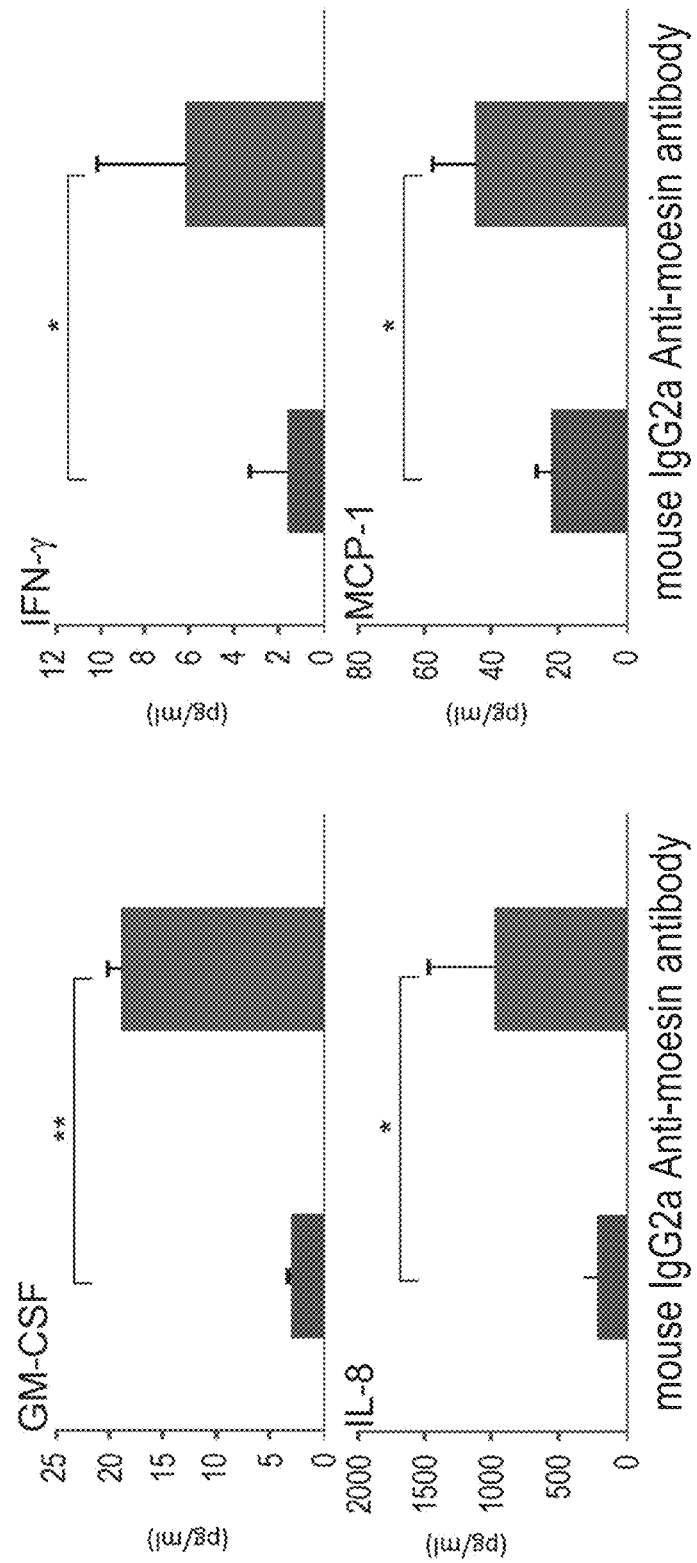
FIG. 11 is graphs showing the results that were obtained in Example by measuring the production profiles of cytokines and chemokines in neutrophils of healthy subjects upon stimulation with an anti-moesin antibody.

As shown in FIG. 11, the culture supernatant collected 24 hours after the stimulation of neutrophils with the anti-moesin antibody exhibited a high value for MCP-1 and IL-8. From this, it was suggested that the anti-moesin antibody and IL-8 interact with each other in vivo. Here, IL-8 is a cytokine which is chemotactic for neutrophils and enhances inflammation by increasing the migration of neutrophils to the site of inflammation and the recruitment of neutrophils into blood. That is, it was shown that the anti-moesin antibody activates neutrophils to induce the production of the inflammatory cytokine.

14. Measurement of the Cytokine and Chemokine Production by Monocytes of Healthy Subject Upon Stimulation with Anti-Moesin Antibody Since the anti-moesin antibody was found to react with monocytes, in the same manner as described in the above, the production profiles of cytokines and chemokines were measured upon stimulation of monocytes with the anti-moesin antibody and the reaction to the stimulation of neutrophils with the anti-moesin antibody was analyzed in vitro.

First, PMBCs (peripheral blood mononuclear cells) were isolated and suspended in 10% FBS/RPMI at a concentration of $2 \times 10^6$ cells/ml.

Thereafter, 100 μL of the thus obtained PBMC suspension was inoculated in each well of a 96-well plate. Then, after incubating the plate in a $CO_2$ incubator at 37° C. for 2 hours, the resulting plate was washed with PBMC twice and the cells remaining in the wells were used as adhesive monocytes in the following experiment.

To each of the wells containing the thus obtained adhesive monocytes, 200 μL of a mouse monoclonal anti-moesin 2287 antibody (10 μg/ml) was added, and after incubating the plate in a $CO_2$ incubator at 37° C. for 24 hours, the resulting plate was centrifuged at 1,000×g and 20° C. for 10 minutes to recover supernatants.

Using the thus obtained supernatants, the production amounts of various cytokines and chemokines were measured using a multiple cytokine assay kit (Bio-Plex). As for a control group, the same experiment was carried out using a mouse monoclonal antibody IgG2a in place of the mouse monoclonal anti-moesin 2287 antibody. The results are shown in FIG. 12.

Figure 12:
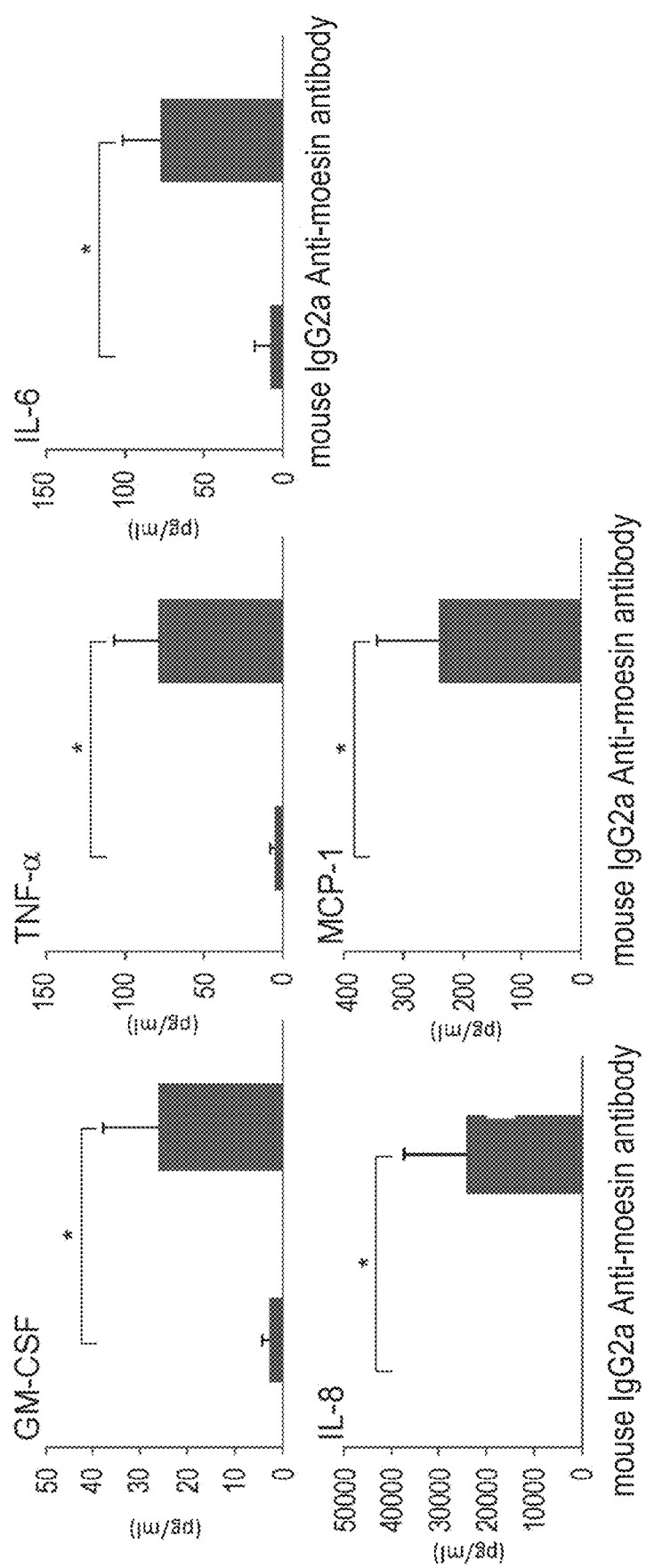
FIG. 12 is graphs showing the results that were obtained in Example by measuring the production profiles of cytokines and chemokines in monocytes of healthy subjects upon stimulation with an anti-moesin antibody.

As shown in FIG. 12, in the culture supernatant collected 24 hours after the stimulation of monocytes with the anti-moesin antibody, an increase was observed in a number of inflammatory cytokines such as GM-CSF, TNF-α, IL-6, IL-8 and MCP-1, in addition to the cytokines that had a significantly higher value in the group of patients who were positive for the anti-moesin antibody. From this, it was thought that the anti-moesin antibody plays a role in the induction of various inflammations by interacting with a number of inflammatory cytokines in vivo. Accordingly, in angiitis patients, it is believed possible to further subclassify angiitis from a different viewpoint by not only detecting the presence or the amount of an anti-moesin antibody (autoantibody) in a biological sample, but also measuring the production profiles of various cytokines and chemokines that are produced by the anti-moesin antibody. That is, according to yet another embodiment of the present invention, use of a production profile of a cytokine and/or a chemokine in a monocyte and/or a neutrophil, which is obtained by stimulation of the monocyte and/or the neutrophil with an anti-moesin antibody, for subclassification of angiitis is also provided. Accordingly, the specificity of the testing method of angiitis provided by the present invention is further improved, so that a technology which is highly advantageous as a diagnostic method of angiitis is provided.

The invention claimed is:

1. A method for testing a subject for angiitis, which comprises (a) contacting a biological sample from a subject with a test reagent for detecting an antibody specifically recognizing moesin and a test reagent for detecting an antibody specifically recognizing myeloperoxidase in said sample, and (b) detecting the antibody specifically recognizing moesin and detecting the antibody specifically recognizing myeloperoxidase in said sample, wherein when the antibody specifically recognizing moesin and the antibody specifically recognizing myeloperoxidase is detected in said sample, said subject has angiitis.

2. The method according to claim 1, wherein said biological sample is a serum sample and said antibody is an autoantibody to moesin.

3. The method according to claim 1, wherein said angiitis is microscopic polyangiitis, allergic granulomatous angiitis (Churg-Strauss syndrome), Wegener's granulomatosis, Guillain-Barré syndrome, thrombotic thrombocytopenic purpura (TTP), idiopathic thrombocytopenic purpura, IgA nephropathy, rapidly progressive glomerulonephritis, idiopathic interstitial pneumonia, sarcoidosis, diffuse panbronchiolitis, Behçet's disease, systemic lupus erythematosus (SLE), Sjögren's syndrome, Takayasu's disease (aortitis syndrome), Buerger's disease, polyarteritis nodosa, malignant rheumatoid arthritis, temporal arteritis, antiphospholipid antibody syndrome, scleroderma, eosinophilic fasciitis or pemphigus.

4. The method according to claim 1, wherein said angiitis is microscopic polyangiitis.

* * * * *